(12) United States Patent
Foster et al.

(10) Patent No.: US 8,541,735 B2
(45) Date of Patent: Sep. 24, 2013

(54) INLAID OPTICAL MATERIAL AND METHOD OF MANUFACTURE

(75) Inventors: John S. Foster, Santa Barbara, CA (US); John C. Harley, Santa Barbara, CA (US); Ian R. Johnston, Northampton (GB); Jeffery F. Summers, Santa Barbara, CA (US)

(73) Assignee: Innovative Micro Technology, Goleta, CA (US)

( * ) Notice: Subject to any disclaimer, the term of this patent is extended or adjusted under 35 U.S.C. 154(b) by 484 days.

(21) Appl. No.: 12/662,237

(22) Filed: Apr. 7, 2010

(65) Prior Publication Data

US 2011/0250092 A1     Oct. 13, 2011

(51) Int. Cl.
| | |
|---|---|
| *H01L 21/00* | (2006.01) |
| *B29D 11/00* | (2006.01) |
| *H01J 3/14* | (2006.01) |
| *G01N 21/00* | (2006.01) |
| *G01N 15/06* | (2006.01) |

(52) U.S. Cl.
USPC ............. 250/216; 250/573; 438/29; 438/31; 438/32; 438/50; 438/69; 216/13; 216/24; 216/26; 422/73; 422/82.05; 422/82.11

(58) Field of Classification Search
None
See application file for complete search history.

(56) References Cited

U.S. PATENT DOCUMENTS

| | | | | |
|---|---|---|---|---|
| 5,578,528 | A  * | 11/1996 | Wuu et al. .................... | 216/2 |
| 7,220,594 | B2 | 5/2007 | Foster et al. | |
| 7,229,838 | B2 | 6/2007 | Foster et al. | |
| 2005/0282151 | A1 * | 12/2005 | Foster et al. ................. | 435/4 |

* cited by examiner

*Primary Examiner* — Neil N Turk
(74) *Attorney, Agent, or Firm* — Jaquelin K. Spong

(57) ABSTRACT

An optical material is inlaid into a supporting substrate, with the top surface of the optical material flush with the top surface of the substrate, wherein the optical element is used to shape a beam of light travelling substantially parallel to the top surface of the substrate, but with the central axis of the beam below the top surface of the substrate. The optical elements serve to shape the beam of light for delivery to or from a microfabricated structure within the device.

17 Claims, 19 Drawing Sheets

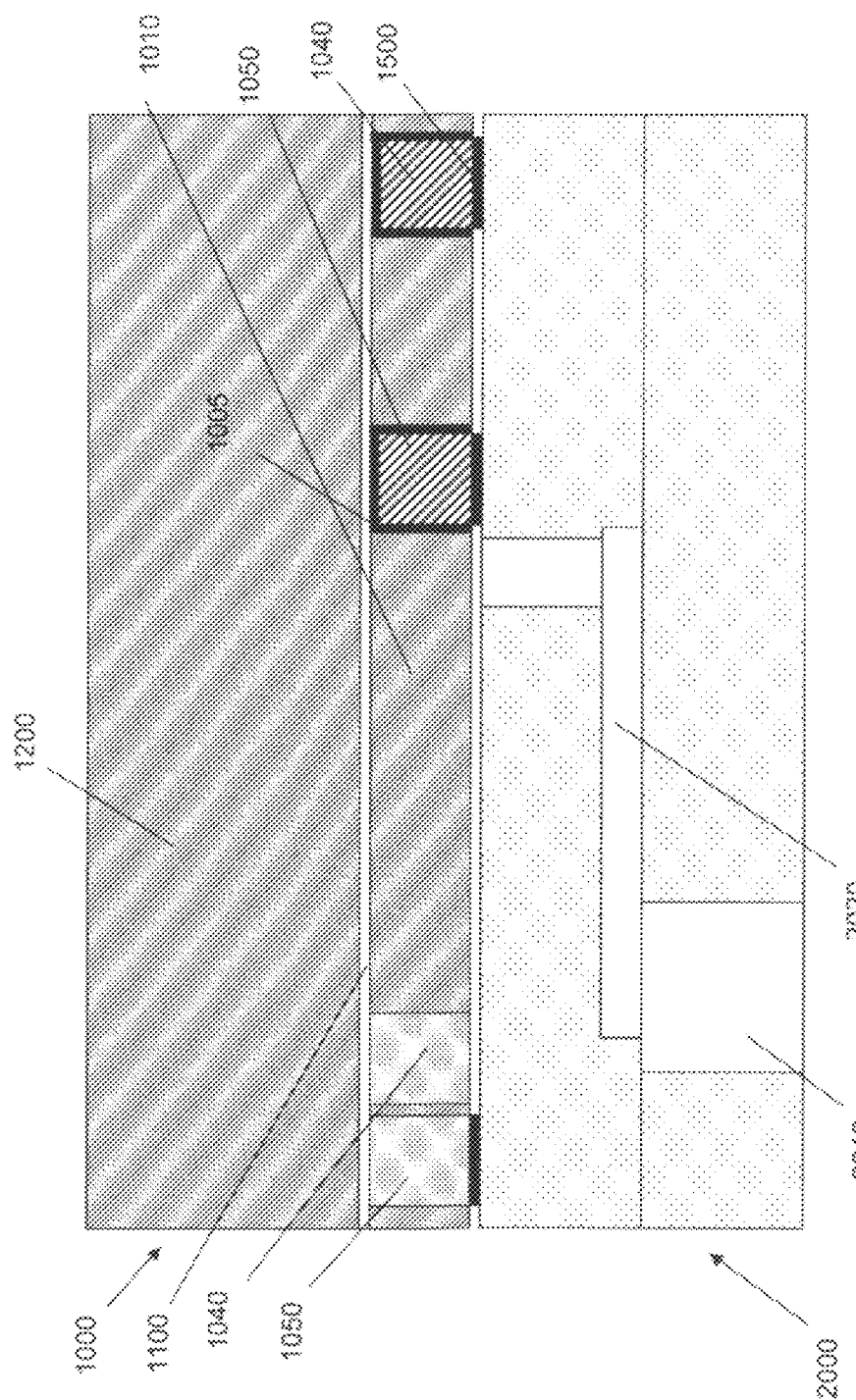

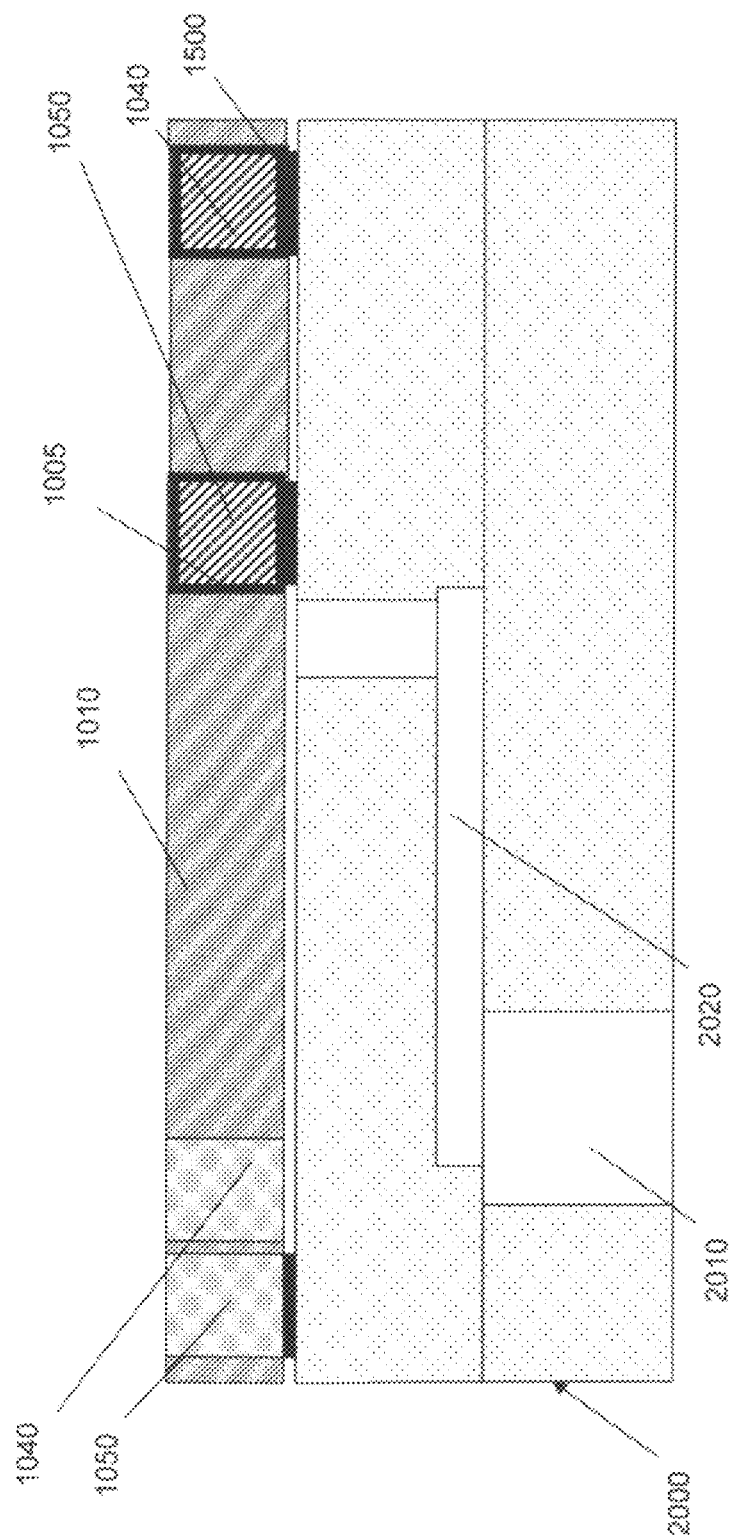

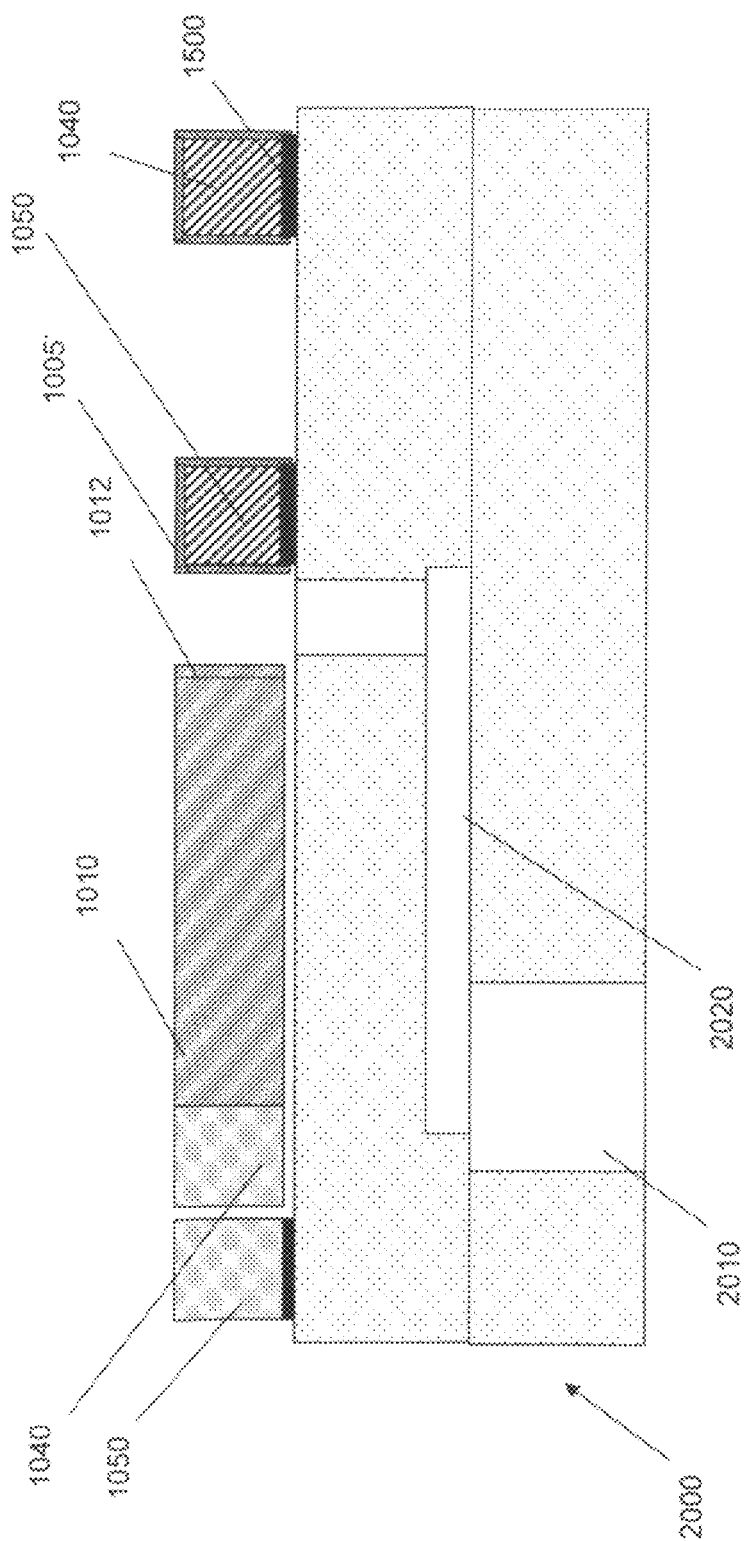

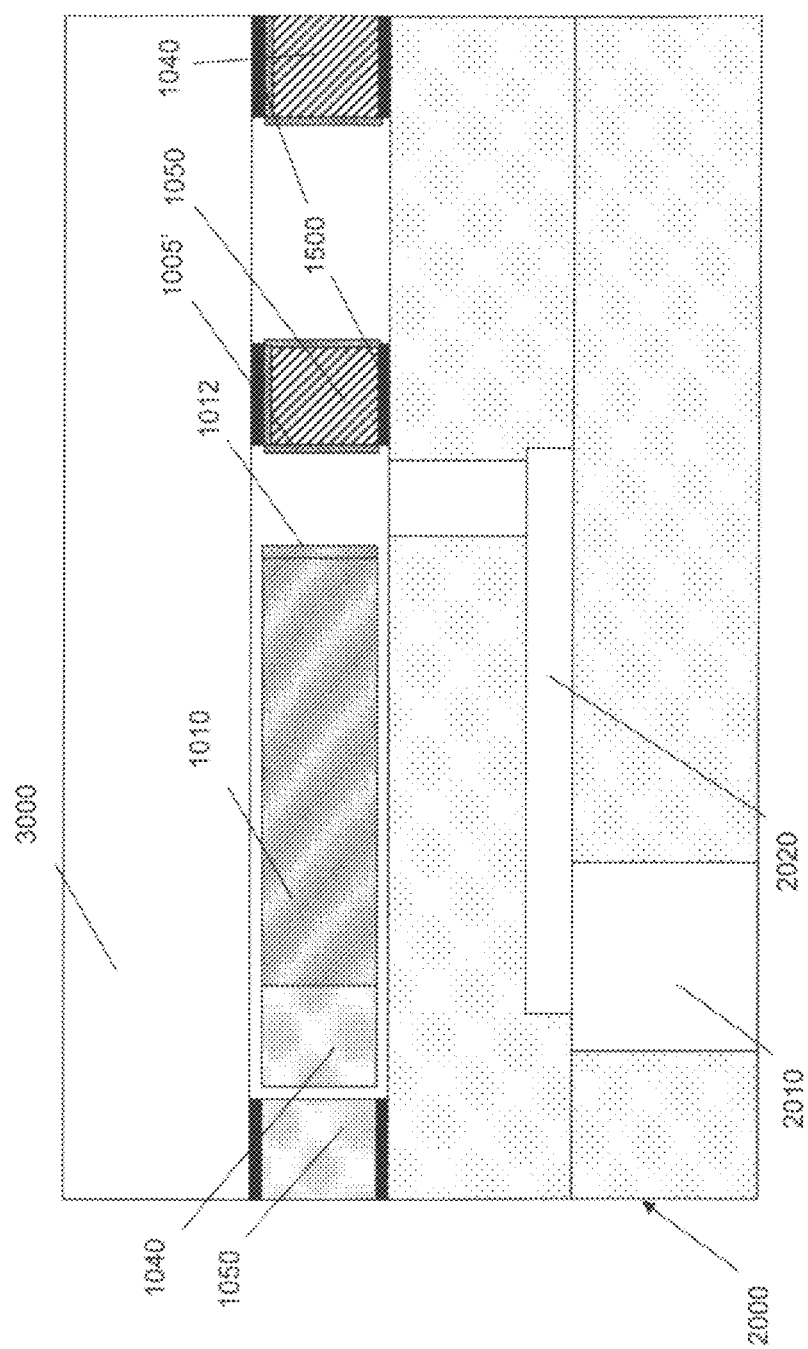

INLAID OPTICAL MATERIAL AND METHOD OF MANUFACTURE

CROSS REFERENCE TO RELATED APPLICATIONS

This U.S. patent application is related to U.S. patent application Ser. No. 11/196,291 filed Aug. 5, 2005, now U.S. Pat. No. 7,220,594 and U.S. patent application Ser. No. 11/260,367 filed Oct. 28, 2005, now U.S. Pat. No. 7,299,838, both assigned to Innovative Micro Technology, the same assignee as the present application. These patents are incorporated herein by reference in their entirety for all purposes.

STATEMENT REGARDING FEDERALLY SPONSORED RESEARCH

Not applicable.

STATEMENT REGARDING MICROFICHE APPENDIX

Not applicable.

BACKGROUND

This invention relates to the formation of an inlaid optical material for shaping a beam of light within a device substrate.

Microelectromechanical systems (MEMS) are devices often having moveable components which are manufactured using lithographic fabrication processes developed for producing semiconductor electronic devices. Because the manufacturing processes are lithographic, MEMS devices may be made in very small sizes, and in large quantities. MEMS techniques have been used to manufacture a wide variety of sensors and actuators, such as accelerometers and electrostatic cantilevers.

MEMS techniques have also been used to manufacture movable actuators of small size, generally using an electrostatic, piezoelectric or less commonly, electromagnetic actuation means to activate a movable member. MEMS devices often make use of silicon-on-insulator (SOI) wafers, which are a relatively thick silicon "handle" wafer with a thin silicon dioxide insulating layer, followed by a relatively thin silicon "device" layer. In the MEMS devices, a thin movable member may be formed in the silicon device layer, and a cavity is created adjacent to the thin beam, typically by etching the thin silicon dioxide layer below it to release the movable member.

A number of MEMS devices use or manipulate light, for example, mirrors, electrooptical transducers, infrared emitters and receivers and spectrum analyzers. In a MEMS display or projector, the movable member may be used to adjust the position of one of many optical elements, such as a tiltable mirror. Such devices typically employ also macroscopic optical elements disposed in space around the MEMS device, to shape the characteristics of the emitted or received light. The inclusion of these elements greatly adds to the overall volume taken up by the systems, increasing its cost and rendering it vulnerable to shock and vibration. For at least these reasons, MEMS based optical systems are not generally mounted on moving systems, such as vehicles, or weapons systems such as missiles or munitions, or in medical devices such as catheter-based surgical or imaging systems.

SUMMARY

Therefore a need exists for a fabrication technique that improves the cost, complexity and robustness of MEMS devices requiring optical components. As described below, techniques are set forth for forming the optical components with an optical material inlaid directly into the silicon substrate. These techniques eliminate the need for a separate optical components, thus reducing cost and complexity and improving robustness to shock and vibration. The inlaid material may also improve the performance of the MEMS device by improving the collection efficiency of emitted light.

The incorporated '367 patent, assigned to Innovative Micro Technology, the same assignee as the present invention, describes an application which may make use of the techniques disclosed herein. These patents described a MEMS-based particle sorting chip, which may be used to separate a particular target cell, such as a blood stem cell, from a fluid mixture. The MEMS particle sorting device of the '594 and '838 patents use reflective and refractive surfaces formed in an optically transmitting layer deposited overtop of a MEMS actuator. These optical elements focus laser excitation light in a detection region of the particle sorting chip. A plurality of MEMS actuators disposed downstream of the detection region direct the particles of interest into one of a plurality of exit paths. A particle of interest is detected by irradiating a fluid stream in the detection region of the optically transmitting layer, and detecting the resulting fluorescence emanating from the particle of interest.

Using the techniques disclosed herein, the optically transmitting layer may be eliminated, and replaced with the optical material inlaid directly into the silicon substrate which supports the MEMS actuator. This may lead to simpler fabrication processes, cost savings and improved performance of the device. It may also reduce the number of tight turns in the flow path, reducing the stress on the living cells and reducing the tendency of the device to clog.

Although embodiments are described which are directed to the MEMS particle sorting device, it should be understood that this embodiment is exemplary only, and that these techniques may be applied to any other device which can make use of beam shaping optics. Such alternative embodiments include cell counters and detectors, which count the number of certain types of cells, such as cancer cells, in a patient sample. The alternative embodiments may also include emitters, detectors, electrooptic transducers, displays and projectors.

BRIEF DESCRIPTION OF THE DRAWINGS

The present invention will be understood more fully from the following detailed description, and from the accompanying drawings, which however, should not be taken to limit the invention to the specific embodiments shown but are for explanation and understanding only.

FIG. 16 is a cross sectional view of a fourth step in an exemplary method of fabricating the device shown in FIG. 12;

FIG. 17 is a cross sectional view of a fifth step in an exemplary method of fabricating the device shown in FIG. 12;

FIG. 18 is a cross sectional view of a sixth step in an exemplary method of fabricating the device shown in FIG. 12; and FIG. 19 is a cross sectional view of a final step in an exemplary method of fabricating the device shown in FIG. 12.

DETAILED DESCRIPTION

The systems and methods set forth herein are described with respect to a particular embodiment of the optical inlay method, directed to a cell sorter for sorting particular cells from a sample of human blood. However, it should be understood that the systems and methods for the optical inlay may be applicable to a wide range of MEMS applications, wherein it is desired to shape a beam of light for manipulation by the MEMS device.

The first embodiment directed to the MEMS cell sorting device will be described in detail first, followed by a description of the optical inlay as applied to the cell sorter and then the fabrication techniques suitable for forming the optical inlays.

Figure 1:
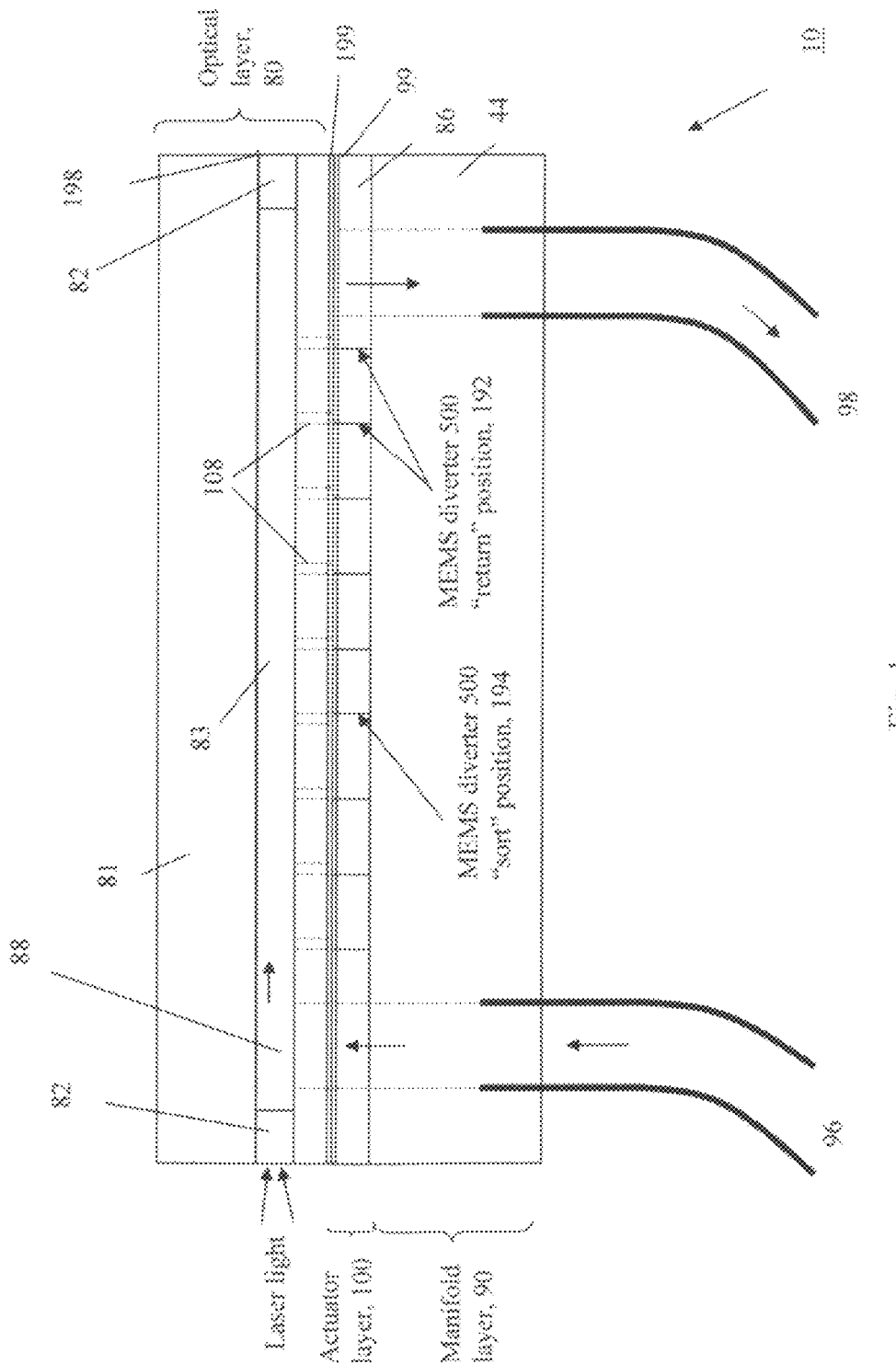
FIG. 1 is a simplified side view of the MEMS particle sorting chip, showing the light channel layer and reflective layers in detail.

The exemplary MEMS cell sorting device is shown schematically in FIG. 1. The MEMS cell sorting device may accept a fluid sample through inlet port 96, which then flows through a horizontal channel 88, before entering a number of parallel vertical channels 108. The parallel channels may have a diameter just large enough to allow the passage of the cell which is the component of interest in the fluid sample. At the exit from each parallel channel is an independent valve/actuator 500. The actuator directs the cells individually into one of two of different possible pathways, which are microfluidic channels etched into the wafer, beneath the parallel channels. The figure shows the application of the device to the separation of a particular component, here blood stem cells, in human blood from a fluid mixture of other cells. The actuator separates the sample stream into one of two manifolds, depending on the detection of a laser-induced fluorescence signal from the components of the mixture. Photons emitted from a fluorophore or multiple fluorphores may indicate that the target particle, or stem cell, is present, and the actuator may direct the cell into a sort manifold with its sort receptacle.

In one embodiment, the fluid mixture enters through the inlet via, it may flood the optically transparent layer 88 which lies between the optical cover 81 and the active layer substrate 44. In this embodiment, optically transparent layer 88 may be sandwiched between two reflecting layers, light reflecting layers 198 and 199. The function of the optically transparent layer 88 is to guide laser light in a quasi-two-dimensional sheet, exposing the cells in the fluid mixture only before the cells fall into the parallel channels 108. Alternatively, the fluid mixture may be transported by a plurality of well-defined fluid paths formed in the optically transparent layer 88 to the tip, or diverter 510 of each actuator 500. In this case, the fluid path may route a portion of the flow from sample input 96 to each one of the parallel channels 108, for example. The optically transparent layer 88 may also include optical elements to further focus the light in the plane of the optically transparent layer 88, as described further in the '367 patent and described briefly below.

The actuators are shown schematically as the plurality of MEMS structures 500, lying at the exit of each parallel channel in FIG. 1. Each of the actuators 500 shown is in the "waste" or "sort/save" positions 192, directing the cells into the waste manifold 110, with the exception of actuator 194, which is in the sort/save position. This actuator directs a fluorescing cell into the stem cell manifold 93, and the remaining actuators 192 direct non-fluorescing cells into the waste manifold 110. After being properly herded into the stem cell manifold, the cell follows the fluid stream under positive pressure, until it reaches the stem cell out tube 104 leading to the stem cell receptacle, or the waste out tube 106 leading to the waste receptacle if it is a non-fluorescing cell. The dual manifolds have been patterned in the MEMS substrate using standard techniques, such as ething, to form the fluid channels. The manifolds may be sealed at the top by a top layer 99, which may be a eutectic or polymer bonding layer, and may lie between bottom light reflecting layer 199 and the MEMS actuator layer 186.

A computer may direct the operation of the various electronics units including the laser, actuator and the detector used to detect the fluorescence emanating from the target cell. The computer may be responsible for the timing of the movement of the actuator 500 to sort the desired cell while rejecting others.

Figure 2:
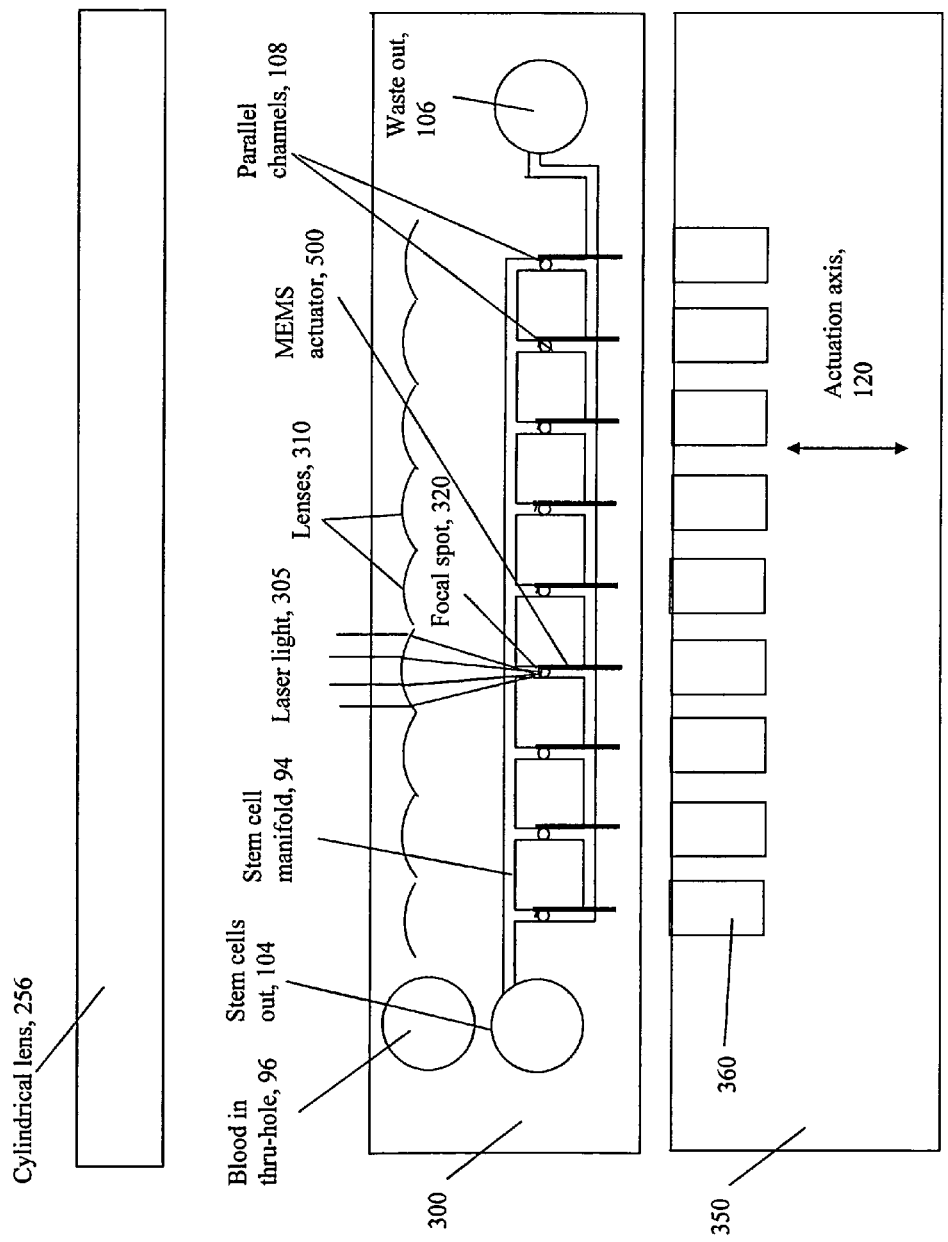
FIG. 2 is a plan view of the top surface of the MEMS particle sorting chip, showing the optically transparent light channel layer, as seen through the optical cover.

The plurality of parallel channels and actuators may be a one-dimensional 1×32 array, arranged in a line as shown in the plan view of FIG. 2. The one-dimensional array allows the laser light to be brought from a line focus to a focus at a plurality of single points, which may have advantages in terms of the timing of the movement of the microactuators 500. Additional details of the structures and method of fabrication of the optical elements used to focus the laser light may be found in the incorporated '367 patent.

In this embodiment shown in FIG. 2, laser light 305 may enter the one-dimensional MEMS particle sorting chip 330 in substantially a single plane, and pass through one of a set of lenses 310. In this plan view, the flow of the fluid is parallel to the paper surface while the fluid is in optically transparent layer 88, but perpendicular to the paper while the fluid is in the parallel channels 108.

Lenses 310 may be refractive lenses, and may focus sections the laser light 305 down to, for example, a single spot at a well-defined point 322 prior to the opening of the parallel channel 108. As one exemplary embodiment, lenses 310 may be formed of a transmissive photoresist such as SU8. SU-8 is a high contrast, epoxy-based photoresist developed by IBM of Armonk, N.Y. The index of refraction of SU-8 is 1.5-1.7 from about 380 nm to about 750 nm, and SU-8 may be virtually transparent over this range. The resist may be deposited in a thin sheet over the silicon substrate, where it is patterned to form the optical elements. In addition to lenses 310, the optically transparent layer may be patterned to form other optical elements, such as reflective surfaces as shown in FIG. 3.

Figure 3:
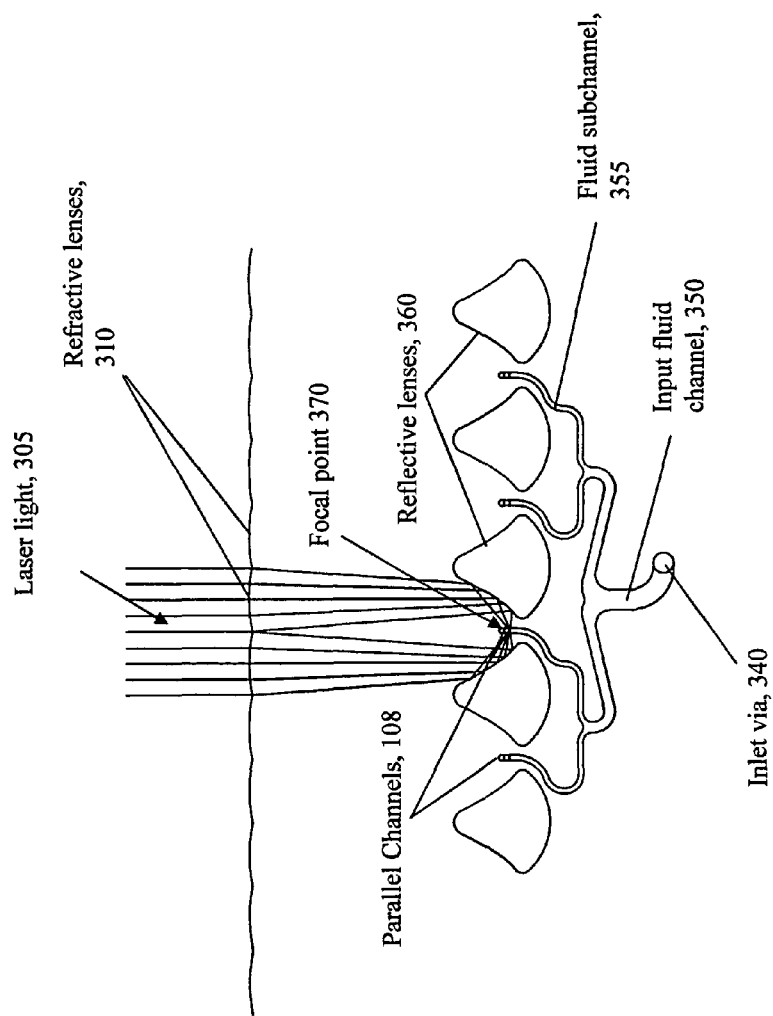
FIG. 3 is a plan view of a one dimensional array of MEMS particle sorters, showing the sorting manifolds, optics and diverter valves.

FIG. 3 shows an exemplary embodiment of an optical system having both reflective and refractive optics on the particle sorting chip 300. As shown in FIG. 3, the sample fluid may enter the optical layer through an input via 340, and may traverse the optical layer to the parallel channels 108 in a confined fluid channel 350. In FIG. 3, the orientation of the axis of the parallel channels is into the paper, similar to the configuration shown in FIG. 2. Therefore, the flow of the fluid is parallel to the paper while the fluid is in the fluid channels 350 and subchannels 355, but perpendicular to the paper while the fluid is in the parallel channels 108. The propagation plane of the laser light 305 is in the plane of the paper.

The laser light 305 may enter the optical layer through a refractive lens 310 before impinging upon a reflective lens 360. For simplicity of manufacture, refractive lens 310 and reflective lens 360 may have the same material interface, such as air/SU-8. The structure designated as 360 may be a void etched in the SU-8, and subsequently filled with ambient air.

As the light rays 305 enter the SU-8 material, they are refracted by the refractive lens surface 310, because the index of refraction of the SU-8 is higher than the index of refraction of air. However, as the light ray travels through the SU-8 layer and impinges on structure 360, because the angle of incidence of the refracted ray may be shallower than the critical angle, and the index of refraction of the SU-8 is higher than that of air, the light ray may be reflected by total internal reflection at the SU-8/air boundary 360. Therefore, this boundary acts as a reflective surface, and may be shaped so that, in combination with refractive surface 310, the light is focused at a point 370 at or near the entrance to one of the parallel channels 108. The refractive lens 310, reflective lens 360 and input channels 350 and 355 may be formed using standard lithographic patterning techniques in a layer of SU-8 photoresist.

Figure 4:
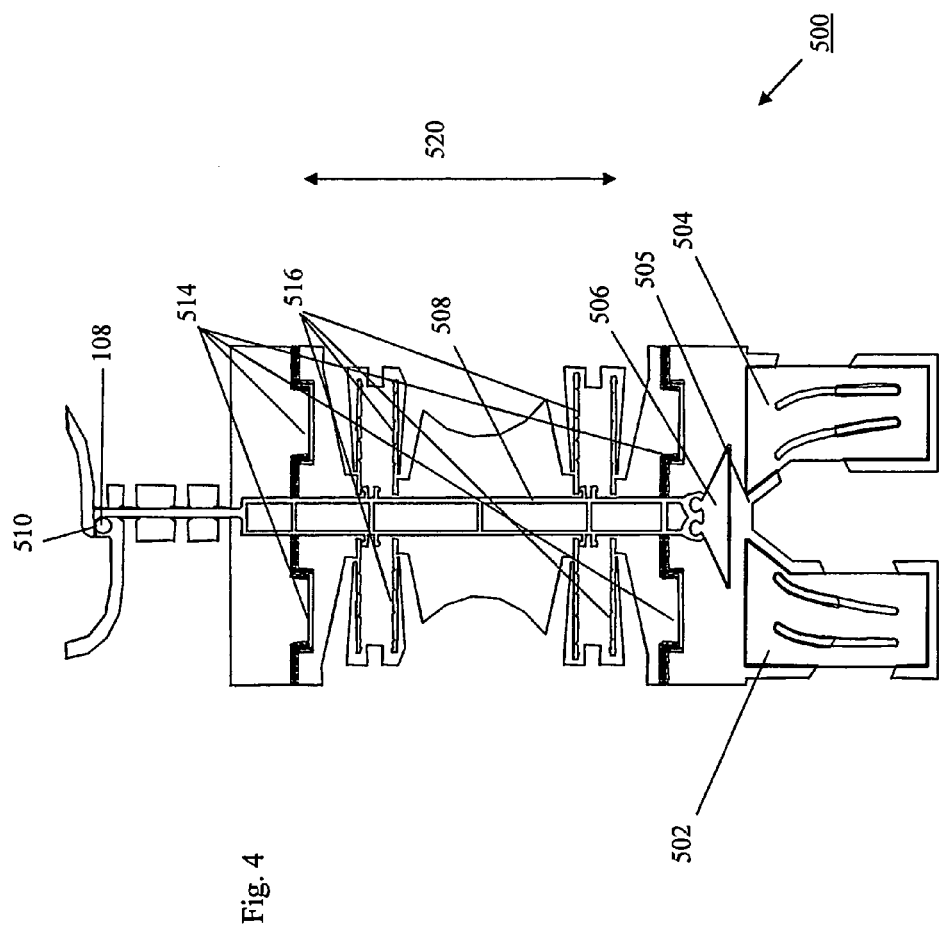
FIG. 4 is a plan view of the MEMS particle sorting actuator in the default position.

FIG. 4 is a schematic illustration showing further detail of the microactuator body portion 500. The microactuator body portion 500 may be extensible/retractable along the axis 520 by interaction with an electromagnetic motor which may be the force-generating portion, not shown in FIG. 4. The force-generating portion may include at least one magnetizable driving core, wound with a coil of wire, which generates magnetic flux which is transmitted to the motor poles 502 and 504. The magnetic flux circulates within the motor poles 502 and 504, and across the small gap, 505 between the microactuator body portion 500 and the motor poles 502 and 504. At the location of the gap 505, the flux extends into the surrounding region and interacts with a magnetizable portion 506 which is affixed to the rigid body 508 of the actuator. The interaction of magnetizable portion 506 with the flux in the gap 505 draws the magnetizable portion 506 into the gap 505, and therefore draws a diverter 510 affixed to the actuator rigid body 508 to a position beneath the parallel channel 108. This changes the direction of flow out of the parallel channel 108 from that shown in FIG. 5.

Figure 5:
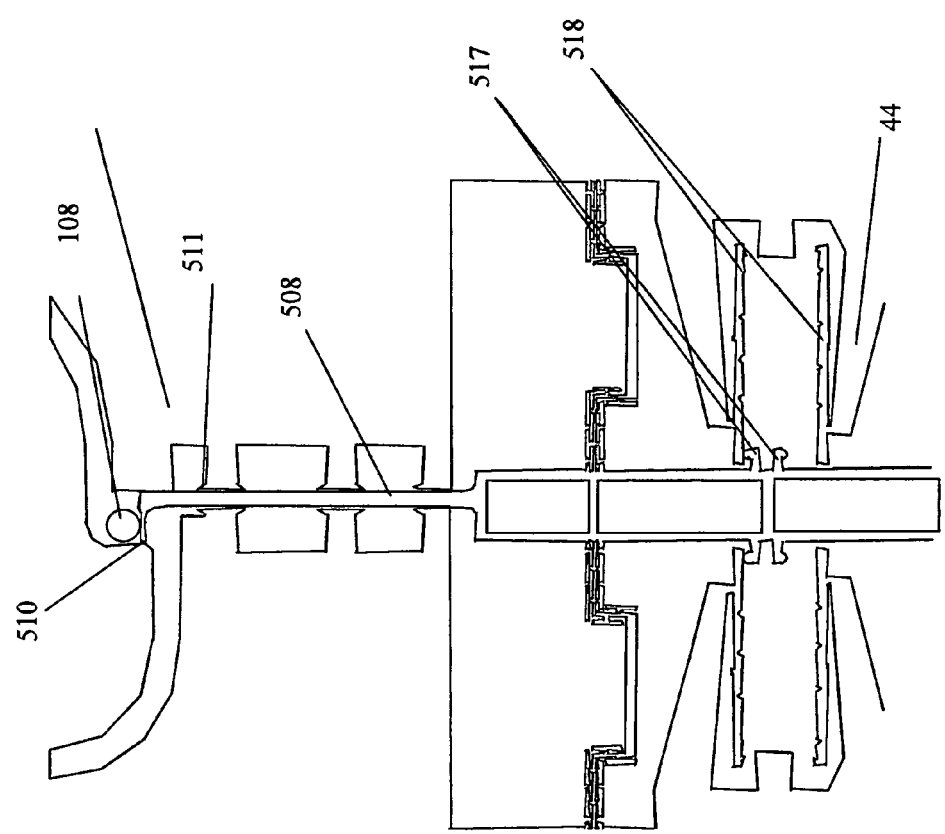
FIG. 5 is a plan view of the MEMS particle sorting actuator in the sort position.

FIG. 4 shows the microactuator body portion 500 in the default position, 92 wherein the diverter 310 of the microactuator body portion 500 directs the fluid stream into the waste/return manifold 312. In FIG. 5 which shows the actuator 500 and diverter 510 in magnification, the magnetizable portion 502 is interacting with the gap 505 between the motor poles 502 and 504, and therefore has been retracted into the gap 505. This retraction pulls the diverter 510 to a position 92 in which it is below the parallel channel 108, and therefore directs the fluid stream into the sort/save manifold 314.

As depicted in FIGS. 4 and 5, the microactuator body portion 300 may also include a set of restoring springs 514, which return the magnetizable portion 506 and rigid body 508 from their actuated position to their default position shown in FIG. 4. Depending on the restoring force of these springs, the actuator 500 may return to its default position within about 10 μsec.

Using otherwise the same architecture as previously described for the MEMS-based cell sorting device, both refractive lens 310 and reflective lens 360 and the entire optically transparent layer 88 may be replaced with an inlaid optical material, which is inlaid into the surface of the device layer of the SOI substrate. Inlaid optical elements may thereby interact with a beam with a beam of light propagating in a plane substantially parallel to the top surface of the substrate. The inlaid optical elements may be fabricated using the novel systems and methods described below, and may offer significant advantages, in terms of process complexity, cost and performance of the device.

Figure 6:
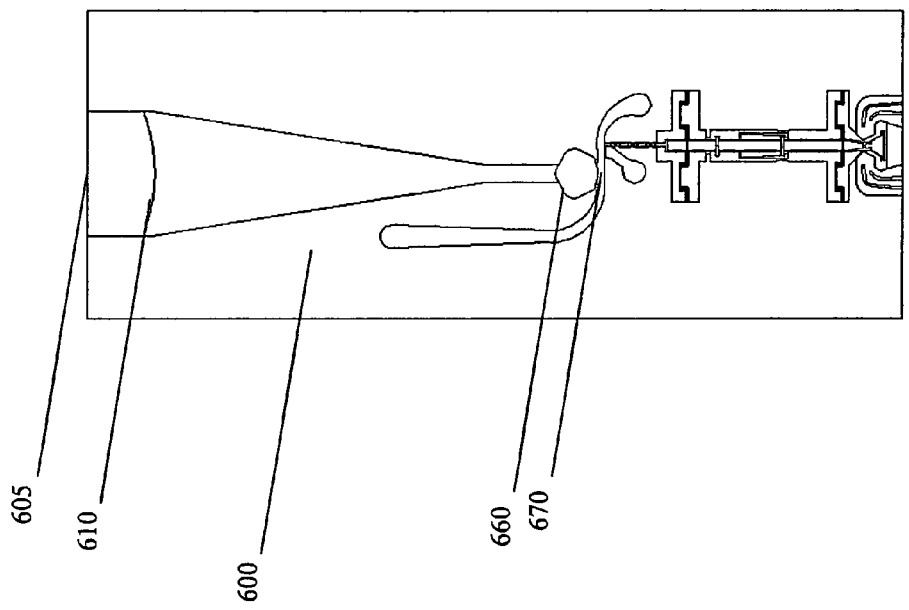
FIG. 6 is a plan view of the MEMS particle sorting actuator with inlaid optical components.

FIG. 6 is a plan view of a portion of the cell sorting system of FIG. 3, where an inlaid optical material replaces reflective and refractive lenses formed in a layer of optically transmissive material. Instead of depositing the optically transmissive material over the surface of the substrate and patterning that layer, voids are formed in the substrate surface and filled with the optically transmissive material. The material is then made flush with the rest of the remaining substrate surface. These steps may be taken before formation of any other needed voids, or of the microactuator 500. As will be described in detail below, the optical material may be inlaid in the surface of the SOI wafer in which the actuator, or other portions of the MEMS device, will later be formed.

FIG. 6 shows two refractive surfaces 610 and 660. The outer edge 605 of optical element 610 may also be considered a reflective surface, although it is not used as such in this embodiment. The space between optical elements 610 and 660 may be a void 615, such that rays passing through surface 610 are bent as they traverse the boundary between the higher index of refraction material to the lower index of refraction material. Similarly, as rays pass through void 615 and enter optical element 660, the rays are bent. For the optical materials described herein, the index of refraction is assumed to be considerably greater than 1, and about 1.5 for the glass materials and SU-8. Because the index of refraction of the optical material is greater than 1, the light rays will be bent upon passage through the boundary, by an amount which can be calculated by Snell's Law:

$$\sin\Theta_2 = \frac{n_1}{n_2}\sin\Theta_1$$

Where $\Theta_1$ and $\Theta_2$ are the angles of incidence with respect to normal incidence, and $n_1$ and $n_2$ are the respective indices of refraction of material 1 and material 2. If the shape of the boundary is properly designed in order to provide, a beam of parallel rays of light may be focused to a point occurring downstream of the lens.

Figure 7:
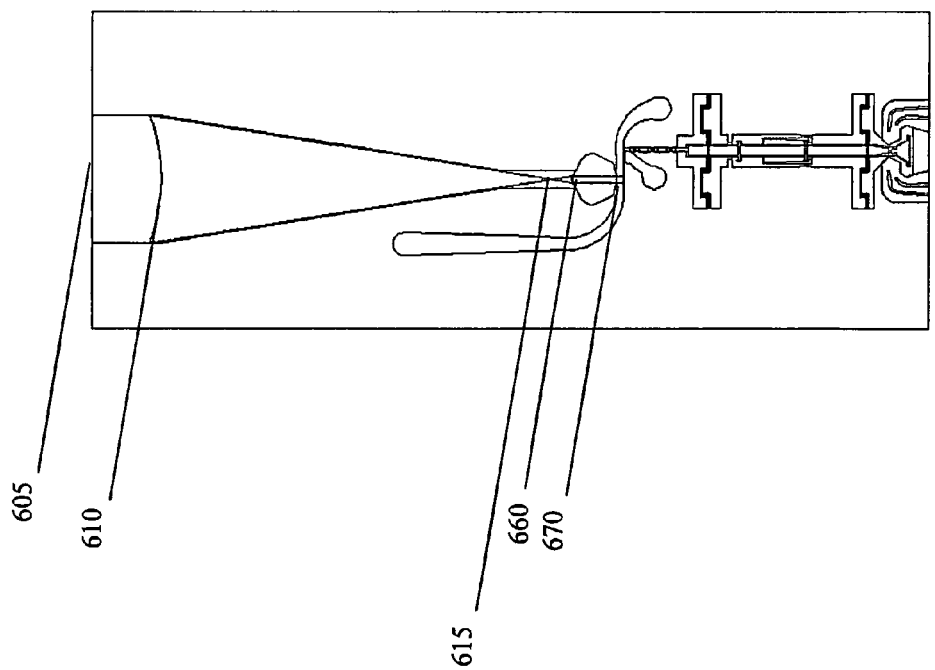
FIG. 7 is a plan view of the MEMS particle sorting actuator with inlaid optical components showing a ray trace diagram through the optical components into the detection region.

Because as described below, the optical structures are formed lithographically, they may have arbitrarily complex shapes. For example, optical elements 610 and 660 may be shaped so as to focus the substantially parallel rays of light propagating parallel to the top surface of the wafer entering optical element 610 at surface 605 to a point, 620 shown in FIG. 7. This point may be within the void 615, and before the second optical element. From this focal point 620, the rays may again diverge until they impinge on the boundary of the second optical element 660. The second optical element 660 again refracts the light rays, and if properly designed, may bend each into a parallel beam of light. This parallel beam may enter a portion of the fluid channel to provide the excitation of the fluorophore molecule. Upon excitation, this molecule will then emit a photon of fluorescence which will be detected by the detector.

The optical elements 610 and 660 may be formed with an inlay process. This process will be outlined briefly here with reference to FIGS. 8 and 9, and applied to two embodiments illustrated in FIGS. 10-11. The process used to form these features 610 and 660 will then described in more detail with reference to FIGS. 12-19.

Figure 8:
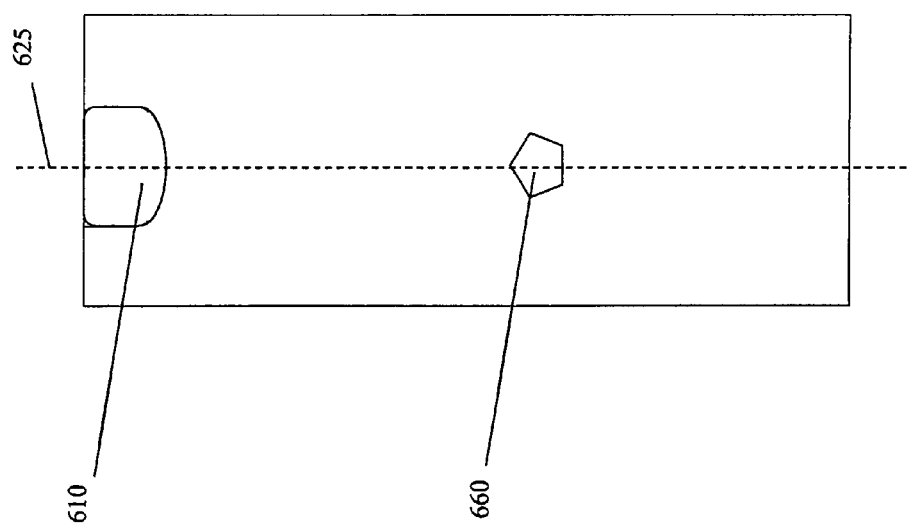
FIG. 8 is a plan view of a substrate with voids formed for deposition of the optical material.
Figure 9:
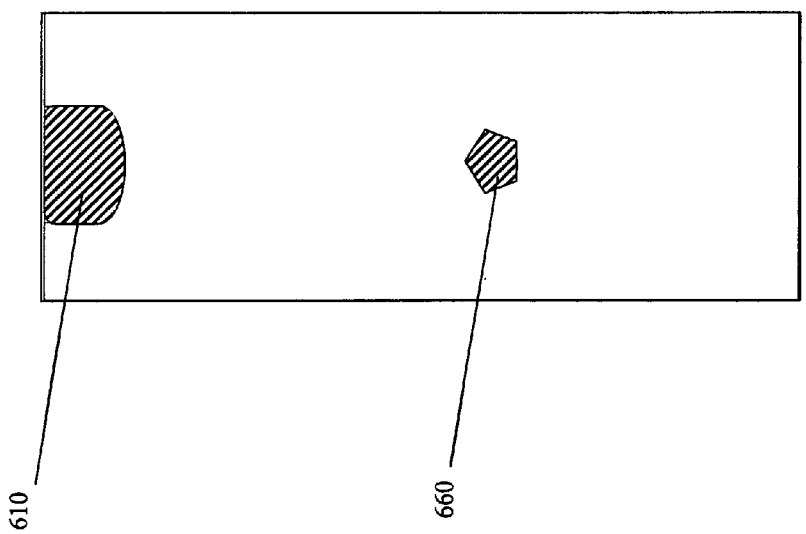
FIG. 9 is a plan view of a substrate with the optical material filling the voids.

To form the optical elements 610 and 660, a void may first be formed in the surface of the substrate. In one exemplary embodiment, the substrate is a silicon-on-insulator (SOI) substrate, in which the actuator or other portions of the device will also be formed. The SOI substrate may consist of a 50 μm device layer, a 5 μm dielectric layer, and a 500 μm thick handle layer. The voids may have the shape of the ultimate optical element. In FIG. 8, these shapes are roughly spherical and pentagonal. However, it should be understood that these shapes are exemplary only, and that a wide variety of other shapes may be employed, to manipulate the characteristics of a light beam travelling substantially parallel to the top surface of the substrate. The shapes of the voids may be the same, or they may be different, as is the case with voids 610 and 660. It should be understood that the formation of two voids 610 and 660 is exemplary only, and that one or more voids may be formed, depending on the geometry and the details of the application.

One aspect of the fabrication of the optical elements that is important for their function, is that the boundaries of the optical material needs to be smooth in order to minimize light scattering at the boundary. This, in turn, requires that the voids 610 and 660 formed in the silicon substrate be smooth-walled. Since the etching process used to create these voids 610 and 660 can leave a rough surface, this surface may be smoothed by allowing an oxide to form on the surfaces, and then stripping the oxide off. The oxide may be formed by baking the substrate in an oven at about 1100 degrees centigrade in an oxygen or water vapor atmosphere for about 2 to about 10 hours to form 1 μm of oxide. The stripping of the oxide can be accomplished by applying a hydrofluoric acid (HF) etchant at room temperature with a concentration of about 50% HF, for up to about 24 hours. This process can be repeated multiple times if additional smoothing is desired.

After formation of the voids 610 and 660, a first optically transmissive material having an index of refraction may be deposited and contained in the voids, wherein a top surface of the optically transmissive material is substantially flush with the top surface of the substrate. The optically transmissive material may form a first optical element, configured to interact with a beam of light propagating in a plane substantially parallel to the top surface of the substrate. The deposition of the optically transmissive material may fill the void to a point somewhat beyond the top surface of the substrate. In this case, the substrate with optically transmissive material inlaid therein may be planarized using an appropriate technique, such as chemical mechanical planarization. In one exemplary embodiment, the first optically transmissive material may be silicon dioxide ($SiO_2$) or glass, both having an index of refraction of about 1.5. This material may be deposited in both of voids 610 and 660, such that both the first optical element and the second optical element comprise the same optically transmissive material, but they shape the light beam in different ways because of their different shapes. For example in FIG. 7 it is shown that both optical elements are refractory, the first optical element bringing the beam to a focal point, the second optical element creating parallel rays after passage of the beam through the focal point.

After deposition and planarization, additional voids 620 may be formed adjacent the first optically transmissive material. These voids 620 may be filled with a second optically transmissive material having a different index of refraction that the first optically transmissive material, and adjacent to the first optically transmissive material. The second optically transmissive material may simply be air, with a refractive index of about 1. The second optically transmissive material may cause the bending of light at the boundary, by at least one of reflection or a refraction of the light.

an interface between regions of varying index of refraction between the optical material (n about 1.5) and air (n about 1), thus allowing the bending of the light rays at the interface. The voids 620 may also provide regions for the focusing of the refracted light to a point 615 within the void 620.

Figure 11:
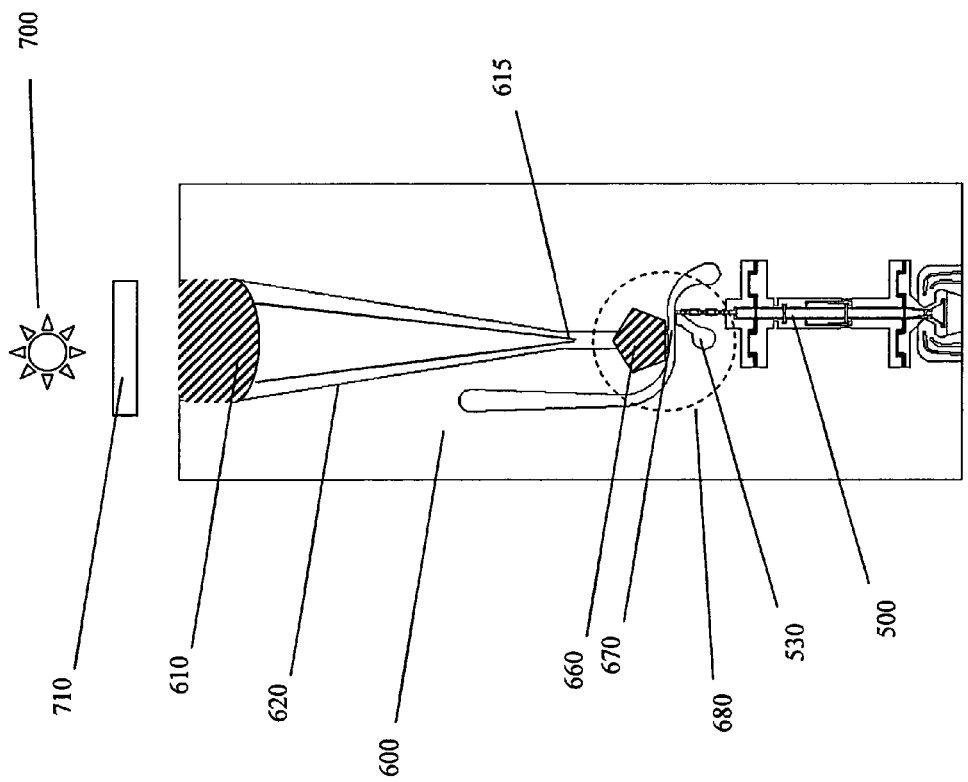
FIG. 11 is a plan view of a substrate with voids formed for shaping of the light beam and fluid channel and including an exemplary MEMS actuator.

Although the optical elements 610 and 660 are shown in FIG. 11 having arbitrary shapes such as a pentagon, it should be understood that this is only for ease of depiction, and that optical elements 610 and 660 may have any shape which is capable of being generated on a photolithographic mask. The shape of optical elements 610 and 660 may be chosen or designed in a way to effectively shape a beam of light to the intended purpose. Such shapes may include spherical, circular, parabolic, hyperbolic, dispersive, reflective and refractive, for example. The optical elements 610 and 660 may perform any of a number of functions on the transmitted light, including diffraction, dispersion, diffusion, reflection, refraction or focusing the beam of light. Hyperbolic lenses, for example, may form the basis of a Powell lens, which is an important means for converting a Gaussian profile laser spot into a "top hat" profile. Other useful shapes may include computer generated shapes that can reduce or eliminate aberrations, diffractive elements, such as gratings, dispersive elements, such as prisms, and birefringent elements, such as polarization rotators. Because the optical elements are configured to interact with a beam of light propagating substantially parallel to the substrate surface, the optical elements may have a symmetry axis 625 which is also parallel to the substrate surface. The symmetry axis 625 may also be collinear with a line bisecting the optical elements as shown in FIG. 8. The symmetry axis 625 may be defined in the plan views (FIG. 8, for example), as the axis running through the element that if the element is folded in half about this axis, the halves are substantially identical.

Optical elements 610 and 660 may have different focal lengths, and may be disposed such that light focused to a spot in the void 620 after the first optical element 610 is reshaped into parallel propagating rays after traveling through the second optical element 660, at which point the light is delivered to the target portion of the microdevice, as described next.

During or after formation of the voids 620, other structures necessary for the functioning of the device may be formed. These other structures may include the target portion of the microdevice, which receives and uses the light shaped by the optical elements 610 and 660. The target portion may be, for example, a microfabricated cell sorter, a cell counter, and optical emitter or an optical detector.

Figure 10:
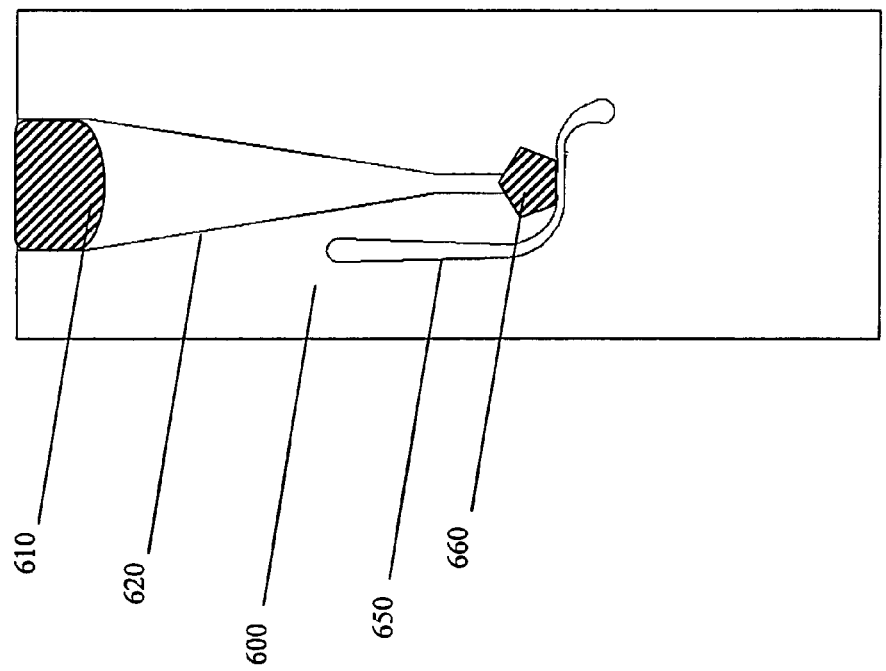
FIG. 10 is a plan view of a substrate with voids formed for shaping of the light beam and fluid channel.

For example, FIG. 10 shows the substrate after formation of a microchannel 650, which is the target portion for this device. This embodiment uses the optical inlaid material to shape a beam of light propagating in a plane substantially parallel to the substrate surface and deliver it to the microchannel 650. The light may emanate from a laser (not shown) having an axis substantially parallel to the top surface of the substrate The microchannel 650 may be formed having a width comfortably exceeding the diameter of the largest particle or cell, such that the particles or cells flow freely but substantially in single file through the microchannel. By placing a detector over the top surface of the substrate, a cell counter may be constructed, which counts the number of appropriately tagged cells flowing through the microchannel. Such a cell counter may be useful for the detection of abnormal or cancerous cells, such as cervical cancer cells. A microchannel based cell counter may thereby replace PAP smears in the detection of cervical cancer.

FIG. 11 shows another embodiment of a device using the optical inlay techniques, wherein the target portion of the microdevice is a cell sorter. This embodiment again uses the optical inlay element to shape a beam of light propagating in a plane substantially parallel to the substrate surface. The light may originate from one or more lasers 700, and the light focused to a line by cylindrical lens 710. The light may enter optical element 610 formed in SOI substrate 600. Optical element 610 focuses the light to a point within the cavity 620 to a point as was shown in FIG. 7. From this focal point, the light again diverges and is refracted again by optical element 660. Optical element 660 refracts the light into parallel rays which then enter the detection region 670. The light excites the fluorescent tags which are affixed to the target cells. The fluorescent tags then emit fluorescent radiation which is detected by a detector 680 which is disposed above the surface of the substrate at an angle substantially orthogonal to the surface. Using this arrangement, the amount of laser light scattered into the detector is reduced, thus reducing the noise in the measurement. This may lead to simpler fabrication processes, cost savings and improved performance of the device. It may also reduce the number of tight turns in the flow path, reducing the stress on the living cells and reducing the tendency of the device to clog.

When a fluorescent signal is detected by detector 680, the monitoring computer generates a signal instructing the actuator 500 to be moved, thus directing the target cell into the sort reservoir 530.

FIGS. 12-19 depict an exemplary method for fabricating the inlaid optical elements 610 and 660. It should be understood that this method is exemplary, and may be used to fabricate any of a number of shapes of inlaid optical elements, as well as voids between the optical elements.

Figure 12:
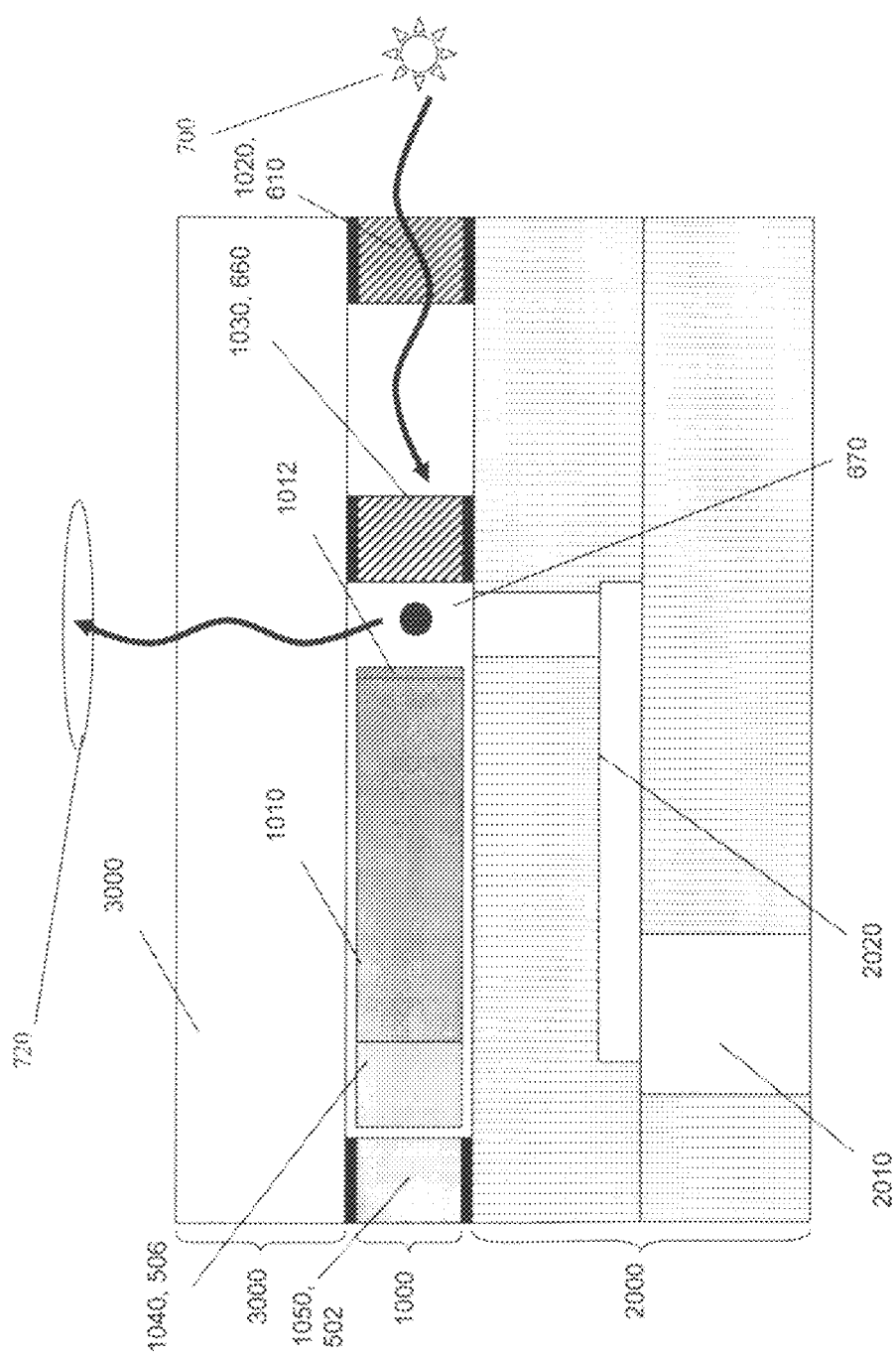
FIG. 12 is a cross sectional schematic view of the device of FIG. 11.

The device is shown first in cross section in FIG. 12. While the numbering scheme in FIGS. 12-19 is changed for internal consistency, it should be understood that element 1010 may correspond to microactuator, and elements 1020 and 1030 may correspond to optical elements 610 and 660, respectively.

The bottom structure 2000 herein referred to as the "manifold layer," may include one or more substrates into which fluidic channels 2010 and 2020 have been formed. Fluidic channels 2010 and 2020 may be formed by plasma etching or deep reactive ion etching through a mask, for example. Fluidic channels 2010 and 2020 serve to provide a sample inlet to the device, and to route the fluid sample to the detection region, sort and waste reservoirs.

The middle structure 1000, herein referred to as the "actuator layer," may be a silicon layer in which the target portions of the device is formed. The term "target portions" as used herein should be understood to mean those portions of the device which are intended to use the illumination delivered by optical elements 610 and 660. The target portions may be, for example, the electromagnetic actuator 500 depicted in FIGS. 4 and 5, or the fluidic microchannels 650 depicted in FIG. 10. In other embodiments, the target portions may be optical detectors, reaction chambers, or light sensitive materials, for example.

The upper structure 3000, herein referred to as the "optical cover," may seal the fluidic channels formed in the middle structure 1000. If the upper structure 3000 is made using an optically transmissive material, the signal generated by the laser excitation from laser source 700 of the fluorophore may be detected by a detector 720. As mentioned previously, detector 720 may therefore be disposed in an orthogonal arrangement with respect to laser source 700, and may correspond to detector 680 illustrated in plan view in FIG. 11.

Figure 13:
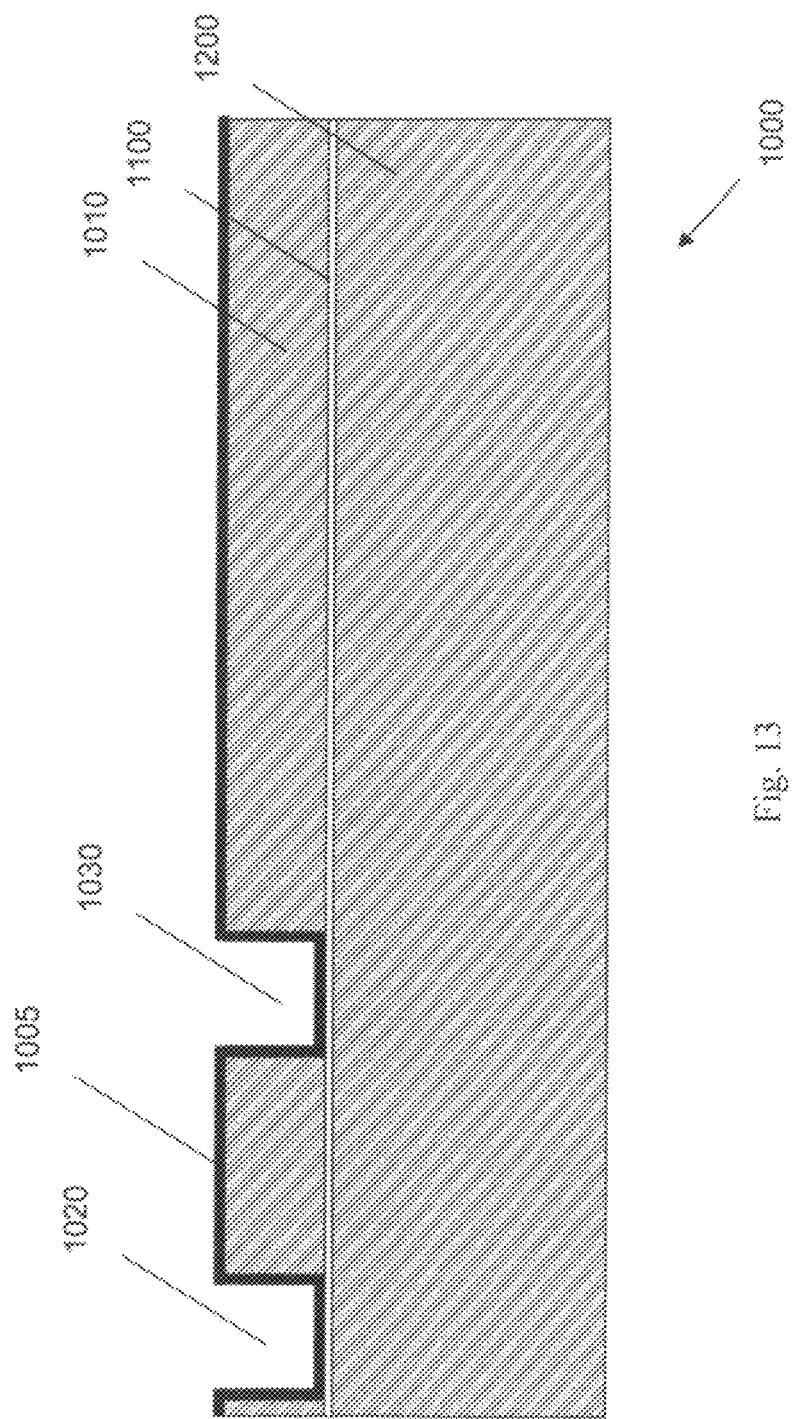
FIG. 13 is a cross sectional view of a first step in an exemplary method of fabricating the device shown in FIG. 12.

An exemplary method for making the structure shown in FIG. 12 will be described with reference to the following FIGS. 13-19. The method begins with the preparation of a substrate 1000 as shown in FIG. 13. Substrate 1000 may be an SOI substrate with a device layer 1010, a dielectric layer 1100, and a handle layer 1200. The handle layer may be quite thick relative to the device layer 1010 and dielectric layer 1100. For example, the handle layer 1200 may be about 500 µm thick, whereas the device layer 1010 may be about 50 µm thick and the dielectric layer 1100 may be about 5 µm thick. Using a standard etching means for removing a portion of the device layer 1010, two voids 1020 and 1030 may be formed in the device layer 1010. Because these voids are formed lithographically using a photolithographic mask, the shapes of voids 1020 and 1030 may be quite complex, such as parabolic or hyperbolic. The formation of these voids will determine the ultimate shape of the optical element, as described further below.

The next step in the exemplary method may be the deposition of a thin layer of conductive material 1005 over the surface of the SOI substrate 1000 and into the voids 1020 and 1030 formed in the surface. Preferably, the deposition is substantially conformal, such as using a sputter deposition, and the conductive material may be, for example, chrome. The function of the conductive material 1005 is to bleed away the charge that will result when other portions of the device layer 1010 of the SOI substrate are removed using an etching process. Without the thin conductive layer 1005, charge would build up on the optical (insulating) material, interfering with the removal of material directly adjacent to the optical material.

Figure 14:
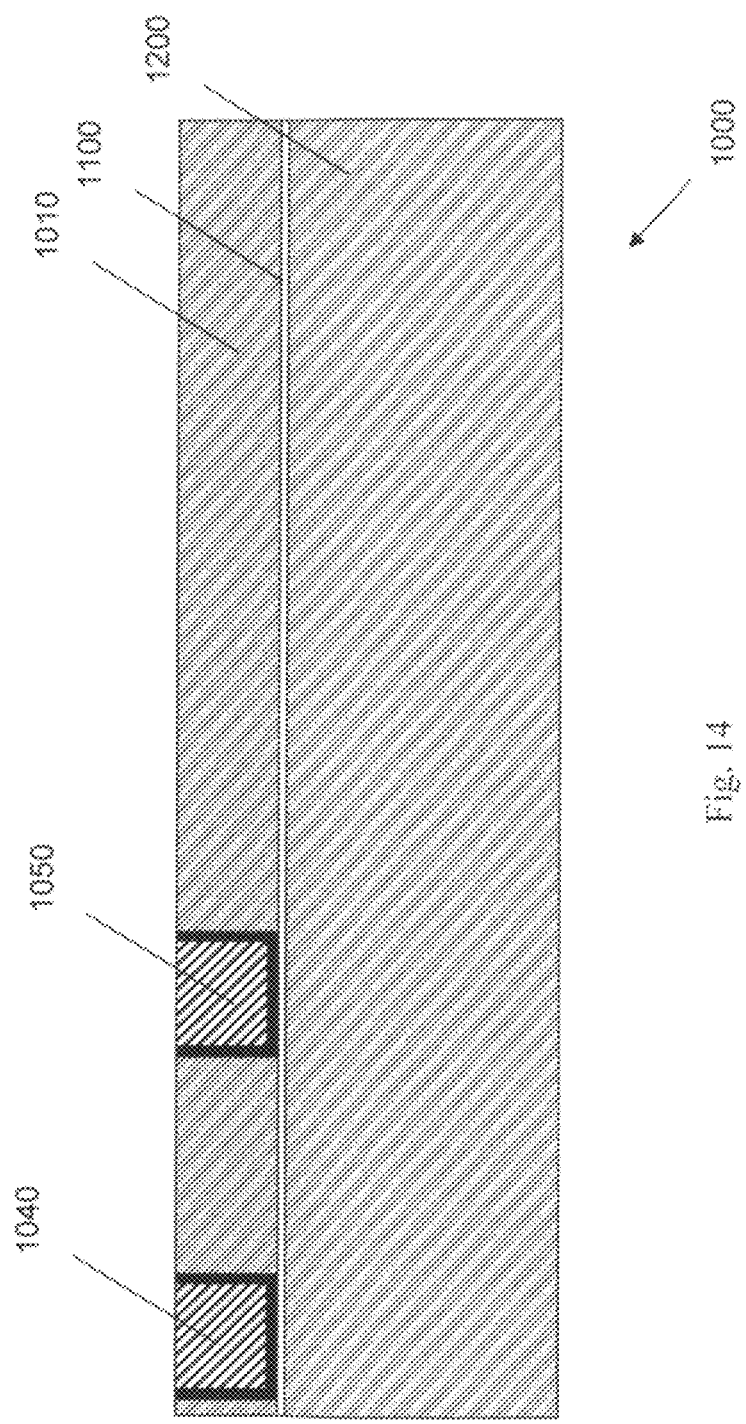
FIG. 14 is a cross sectional view of a second step in an exemplary method of fabricating the device shown in FIG. 12.

After deposition of the conductive material 1005, the optical material is deposited over the surface of the SOI substrate 1000 and into the voids 1020 and 1030, as shown in FIG. 14. Because the optical material will be thick, well over 1 µm, it may be important to use a deposition tool which will minimize the stress in the deposited material. If care is not taken to reduce the stress, delamination of the deposited material may be a problem. In one exemplary embodiment, a radio frequency diode (RFD) deposition tool is used to deposit and optical material, here $SiO_2$ to a depth exceeding 50 µm. Thus, the $SiO_2$ material is deposited within and over the surface of the $SiO_2$ substrate. Excess material may be removed by chemical mechanical polishing (CMP) which will also remove the chromium deposited on the SOI substrate surface. It may be important to render the surface sufficiently flat that a tight seal may be made to an adjacent substrate, to form a leak proof junction to contain the flow of fluid within the microchannels as described later.

Figure 15:
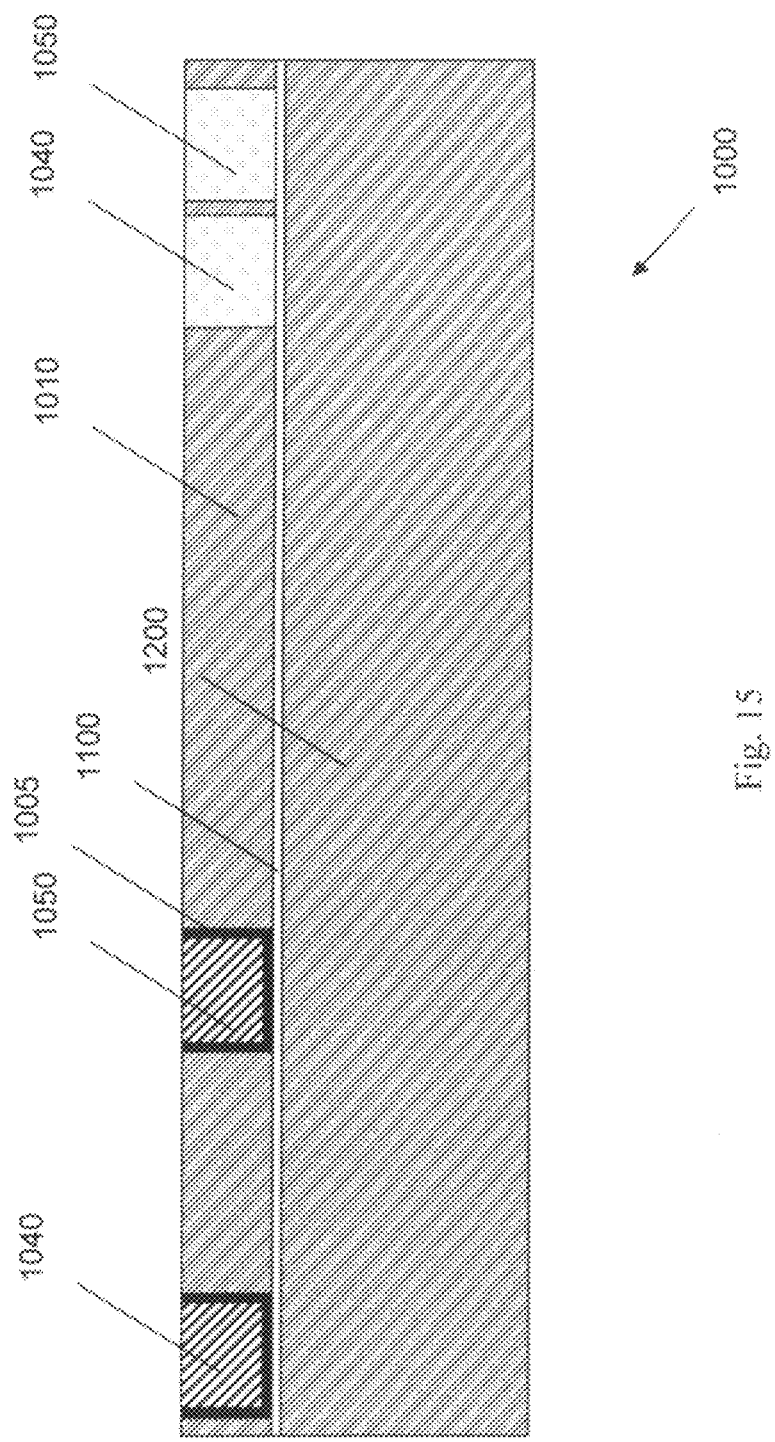
FIG. 15 is a cross sectional view of a third step in an exemplary method of fabricating the device shown in FIG. 12.

The next step in the fabrication process is illustrated in FIG. 15. In this step, a magnetic material, such as NiFe, is deposited in two additional voids 1040 and 1050. These voids 1040 and 1050 may be made using techniques similar to those used for voids 1020 and 1030. NiFe is then deposited into the voids to a depth of 50 μm and lapped flat using CMP. The NiFe may be deposited using a plating process, plating the material onto an appropriately patterned photoresist and seed layer. NiFe portion 1040 may form the magnetizable portion 506 which will be affixed to the actuator body shaft, and NiFe portion 1050 may form the motor poles 502 and 504. Additional details regarding plating of this material may be found in the incorporated '838 patent.

Following the deposition of NiFe, the substrate 1000 may be inverted and coupled to a manifold substrate 2000, as illustrated in FIG. 16. Manifold substrate 2000 may have microfluidic structures formed therein, which accept the input sample and route it to the detection region. As mentioned previously, the microfluidic channel may be formed using any of the well known etching techniques, such as DRIE or plasma etching, with appropriately patterned masks.

The substrates which make up the manifold layer may be any convenient material, preferably one which is biocompatible, so as not to affect the viability of the fluid sample. Silicon or glass substrates may be acceptable. The dimensions of the microfluidic channels may such that they easily admit passage of the cells, for example about 15-25 μm. If the substrates are silicon, they may be fusion bonded together, a technique well known in the art.

The actuator layer 1000 may be coupled to the manifold layer 2000 using a convenient, water proof adhesive 1500, for example, Shin-Etsu SINR negative tone photoresist. After deposition and patterning of the photoresist to cover the areas shown, the wafers are joined and heated to cure the resist, adhering the layers 2000 and 1000. The device in this stage is shown in FIG. 16.

With the silicon handle layer 1030 now at the top of the stack, most of the handle layer may be removed by grinding, as illustrated in FIG. 16. When the grinding has removed all but the last 20 μm of material, the remaining silicon may be removed with a dry, isotropic etch to reveal the oxide layer 1100. The oxide layer may then be removed by, for example, reactive ion etching. The state of the device is now as shown in FIG. 17.

At this point, the actuator 500 and void 620 may be formed in the device. This may be accomplished using standard lithographic procedures: depositing photoresist on the top surface, patterning the photoresist, and then forming the actuator 500 and void 620 using deep reactive ion etching (DRIE) through the silicon device layer 1010. The diverter 1012 (510 in FIGS. 4 and 5) may be formed at the same time and in the same step as the actuator 500. Actuator 500 from FIG. 2 may correspond to reference number 1010 in FIG. 18.

The photoresist (not shown) may be removed from the surface of the silicon device layer using a dry strip process. This process simultaneously oxidizes the layer of chromium 1005, forming a chromium oxide 1005' which is transparent to radiation. Thus, the metal oxide layer 1005' may remain on the optical element 1020 and 1030 without interfering with the operation of the device.

The final step, depicted in FIG. 19, is the coupling of the optical layer 3000 to the wafer stack 1000 and 2000. By selecting an optically transparent material for the optical layer 3000, photons emitted by the fluorophore in the detection region 670 may be transmitted out of the device and to the detector 720 as was shown in FIG. 12. As before with the coupling of the actuator layer to the manifold layer, a photoresist such as Shin-Etsu's SINR may be used as an adhesive compound 1500. The photoresist is applied to the surface and patterned to cover the areas to be joined. The substrates are then joined together and baked in an oven to bond.

While this is one exemplary method, it should be understood that no all of the steps outlined above may be necessary to practice this invention. For example, if a conductive optical material 1020 and 1030 is used, the layer of chromium may not be needed and may be omitted. The steps also need not necessarily be performed in the order described.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. While the embodiment described above relates to a microelectromechanical cell sorter, it should be understood that the techniques and designs described above may be applied to any of a number of other microdevices needed an optical input, such as electrooptic transducers, emitters and detectors. Other optical elements may be envisioned in addition to the focusing elements described herein. Such alternative elements may include dispersive, diffractive, and birefringent elements. The techniques need not be directed to a cell or particle sorter, but may be directed to other microdevices such as cell counters. Furthermore, details related to the specific design features of the microelectromechanical actuator and particle sorting chip are intended to be illustrative only, and the invention is not limited to such embodiments. Accordingly, the exemplary implementations set forth above, are intended to be illustrative, not limiting.

What is claimed is:

1. A microdevice comprising:
  a substrate having a top surface;
  at least one void formed in the top surface;
  a first optical element comprising a first optically transmissive material having an index of refraction and contained in the at least one void, wherein a top surface of the optically transmissive material does not extend beyond the top surface of the substrate and wherein the first optically transmissive material comprises at least one of SiOz, glass, InTiO$_2$, photoresist, and sapphire, and wherein the first optical element is configured to transmit a beam of light propagating in a plane substantially parallel to the top surface of the substrate and has a symmetry axis which is substantially parallel to the top surface; and
  a second optically transmissive material having a different index of refraction and disposed adjacent to the first optically transmissive material, and configured to either reflect or refract the beam of light at a boundary between the first and the second optically transmissive materials, and wherein the second optically transmissive material comprises at least one of air, water and an oil.

2. The microdevice of claim 1, wherein the first optically transmissive material is configured to focus the beam of light to a focal point adjacent to the first optically transmissive material.

3. The microdevice of claim 2, wherein the first and second optically transmissive materials are configured to shape the beam of light and deliver it to a target portion of the microdevice, which receives the beam shaped by the first and second optically transmissive materials.

4. The microdevice of claim 2, further comprising a second optical element comprising the first optically transmissive material contained in a second void formed in the substrate surface, wherein the first optically transmissive material is substantially flush with the top surface of the substrate, wherein the second optical element further shapes the beam of light transmitted through the first optical element.

5. The microdevice of claim 4, wherein the second optical material is substantially the same as the first optical material, and the first and second optical elements are lenses having different focal lengths.

6. The microdevice of claim 3, wherein the target portion of the microdevice is at least one of a microfabricated cell sorter, a cell counter, and optical emitter and an optical detector, and wherein a cover is affixed to the top surface of the substrate, to form at least one fluid channel in the substrate.

7. The microdevice of claim 1, wherein the shape of the first optical element is at least one of circular, parabolic, hyperbolic, dispersive, reflective and refractive.

8. The microdevice of claim 1, wherein the first optical element is configured to perform at least one of diffract, disperse, diffuse, reflect, refract or focus the beam of light.

9. The microdevice of claim 5, wherein the first optically transmissive material is silicon dioxide, the second optically transmissive material is open air, and the first optical element focuses the beam of light to a focal point within the second optically transmissive material, and wherein the first and second optical elements have a symmetry axis which is collinear with a line bisecting the first and second optical elements.

10. The microdevice of claim 9, wherein the first and second optical elements shape the beam of light into parallel rays directed to a detection region of a microfluidic channel.

11. A method for making a microdevice, comprising:
forming a first void in a top surface of a substrate; and
depositing a thin layer of conductive material conformally over the top surface of the substrate and into the first void;
forming a first optical element by depositing a first optically transmissive material having an index of refraction into the first void;
planarizing the top surface of the first optically transmissive material until it is substantially flush with the top surface of the substrate, wherein the first optical element is configured to interact with a beam of light propagating in a plane substantially parallel to the top surface of the substrate; and
forming a second void into the top surface of the substrate, adjacent to and contiguous with the first optical element.

12. The method of claim 11, further comprising:
etching a third void in the top surface of the substrate, configured to transport a volume of fluid from an input reservoir to an output reservoir.

13. The method of claim 12, further comprising:
etching a movable actuator into the top surface of the substrate, configured to separate one component of the fluid from other components of the fluid.

14. The method of claim 12, further comprising:
bonding an optically transmissive second substrate to the top surface of the substrate and over the third void, to form microfluidic channels confining the fluid, but allowing light to pass through to and from the microfluidic channels.

15. The method of claim 14, wherein the substrate comprises a silicon-on-insulator substrate, the optically transmissive second substrate comprises a glass substrate, and the first optically transmissive material comprises silicon dioxide.

16. The method of claim 11, wherein the first optical element is configured to perform at least one of diffract, disperse, diffuse, reflect, refract or focus the beam of light.

17. The method of claim 11, wherein the first optical element has a shape selected from circular, parabolic, and hyperbolic, and a functionality selected from at least one of dispersive, reflective, refractive, diffractive, prismatic, birefringent, and polarization rotating.

* * * * *